United States Patent
Buri et al.

(10) Patent No.: US 6,627,413 B1
(45) Date of Patent: Sep. 30, 2003

(54) METHOD FOR DETERMINING MICROBIAL CONTAMINATION

(75) Inventors: Matthias Buri, Rothrist (CH); Patrick Schwarzentruber, Starrkirch-Will (CH)

(73) Assignee: Omya AG, Oftringen (CH)

( * ) Notice: Subject to any disclaimer, the term of this patent is extended or adjusted under 35 U.S.C. 154(b) by 0 days.

(21) Appl. No.: 09/889,545

(22) PCT Filed: Jan. 17, 2000

(86) PCT No.: PCT/EP00/00328

§ 371 (c)(1),
(2), (4) Date: Oct. 3, 2001

(87) PCT Pub. No.: WO00/46392

PCT Pub. Date: Aug. 10, 2000

(30) Foreign Application Priority Data

Feb. 2, 1999 (DE) .......................... 199 04 057

(51) Int. Cl.$^7$ ............................ C12Q 1/04; C12Q 1/02; C12Q 1/24; C12Q 1/22
(52) U.S. Cl. ............................ 435/34; 435/29; 435/30; 435/31
(58) Field of Search ................ 435/29, 31, 34, 435/39

(56) References Cited

U.S. PATENT DOCUMENTS 6,440,689 B1 * 8/2002 Banks et al. .................. 435/29

* cited by examiner

Primary Examiner—Sandra E. Saucier
(74) Attorney, Agent, or Firm—Jenkins, Wilson & Taylor, P.A.

(57) ABSTRACT

The present invention discloses a process for quantitative and/or qualitative determination of the microbial contamination of suspensions, emulsions or dispersions containing minerals and/or pigments and/or fillers and/or fiber materials wherein following the addition of one or more substances which can be degraded by microorganisms, mixing and optionally subsequent incubation a sample of the suspensions, emulsions or dispersions is centrifuged to separate the microorganisms from the minerals and/or fillers and/or pigments and/or fiber materials and the number and/or size and/or type of the microorganisms is determined in the aqueous supernatant phase after one or more incubations.

28 Claims, No Drawings

METHOD FOR DETERMINING MICROBIAL CONTAMINATION

DESCRIPTION

1. Technical Field

The present invention relates to a process for quantitative and/or qualitative determination of the microbial contamination of aqueous suspensions, emulsions or dispersions containing minerals and/or pigments and/or fillers and/or fiber materials, optionally in combination with polymers in colloidal form.

2. Related Art

Determinations of the germ contamination and hygienic controls of aqueous suspensions by means of conventional methods essentially rely on the propagative capacity of the microorganisms to be detected. Naturally, the time required to perform these methods ranges from 24 h to several days. These time periods are too long for many questions, and the results are obtained too late to intervene in a guiding manner in production processes. Particularly performing controls prior to transport time and again requires methods which are characterized by short determination intervals.

Thus, the main problem of conventional microbiological analyses of aerobic mesophilic germs, such as Plate Count or Easicult, is their long incubation period of up to 48 h. By this methods it is impossible to obtain an evaluation and, thereby, determination of the germ count earlier than after the elapse of two days. In addition, several other effects must be considered such as the nutrient medium, partial pressure of oxygen (aerobic/anaerobic), selectivity, pH and much more.

Therefore, it is often impossible to determine the germ count of products, such as pigment slurries, prior to their shipment to customers and to intervene in a guiding manner by adding biocidal substances. Due to the long transport times required of up to 6 weeks by deep sea ship or rail, the pigment slurry may deteriorate or become unusable. The white pigment slurry may develop a gray color and start to smell. To date, preventive over-dosage of biocidal substances in the pigment slurry is the only possibility to exclude spoilage, is very cost-intensive, dissipates resources, and is ecologically nonsensical. Moreover, two different approaches are necessary to analyze for both aerobic mesophilic germs and fungi. Furthermore, the preparation of serial dilutions is necessary, thus multiplying the number of analyses.

Conventional methods for the determination of germs in the paper and pigment industries have been for example described in the "Schweizerisches Lebensmittelbuch", chapter 56, section 7.01, 1985 edition, 1988 revised version, "Bestimmung von aeroben Bakterien und Keimen", and in the "Schweizerisches Lebensmittelbuch", chapter 56, section 7.22, 1985 edition, 1988 revised version, "Bestimmung von Pilzen". Generally, prior to performing a determination in each case an incubation period of about 48 hours is required.

The CellFacts® particle analyzer and method have been developed by Microbial Systems company, Ltd. More detailed information may be obtained from Labor flash 9/96, Zeitung mit Leserdienst für Labor und Forschung, Ott Verlag+Druck AG, Ch-3607 Thun, Switzerland. Thus, it has been mentioned that the CellFacts analyzer may also be used to carry out determinations of the germ count in calcium carbonate slurries. However, experiments performed in the applicant's laboratory revealed that a determination of this type in the manner described by the manufacturer is impossible or only inaccurate.

The principle of the measurement performed by the CellFacts analyzer is based on the measurement of bacteria, fungi, and yeasts in the form of particles in an electrical field wherein the number of particles is determined by an interval incubation of the samples and subsequent measurement of the increase in particle count and, in the case of exponential growth, by extrapolation to $t_0$. This measurement principle is also effective in measuring a "low" number of "foreign particles" having the same or a similar size as bacteria, fungi, and yeasts. In the case of suspensions and emulsions containing a proportion of "foreign particles", such as minerals, fillers and/or pigments, of >1% by wt. the number of inert "foreign particles" present having the same size as microorganisms, namely 0.5–20 μm, i.e. the blank value $t_0$, is too high to enable the detection of a further increase of the germs by propagation in the incubator within a period of <10 hours. Thus, the CellFacts analyzer is unable to perform a sufficiently exact measurement, and the manufacturer requires a dilution of the starting liquid to ensure applicability.

At a blank value of $10^8$ particles/ml, it is impossible to significantly detect an increase of $10^3$ particles/ml by means of the CellFacts analyzer. However, the dilution required due to the presence of the "foreign particles" is too high so that the dilution of the reproductive organisms which of course are diluted by the same order of magnitude is no longer significant, and the result obtained is incorrect. Furthermore, "foreign particles" having a diameter of >20 μm may plug the measurement cell which has a diameter of only 30 μm. The "foreign particles" may for example be of mineral type, such as calcium carbonate, synthetic, organic, of polymeric type, such as polystyrene acrylate dispersions, or of natural, organic type, such as starch solutions or hemicelluloses and/or cellulose fibers, or a combination of the above particles as they are for example present in a paper mill cycle.

SUMMARY OF THE INVENTION

It is an object of the present invention to provide a quick and powerful, easily performed process for the quantitative and/or qualitative determination of the microbial contamination of aqueous suspensions, emulsions or dispersions containing minerals and/or pigments and/or fillers and/or fiber materials wherein said process avoids the above described disadvantages of the prior art.

According to the present invention, this object has been solved by a process according to the generic part of claim 1 characterized in that a sample of the suspensions, emulsions or dispersions, following the addition of one or more organic substances which can be degraded by microorganisms and optionally following a subsequent incubation, is centrifuged to separate the microorganisms from the minerals and/or fillers and/or pigments and/or fiber materials and the number and/or size and/or nature of the microorganisms in the aqueous supernatant phase is determined after one or more incubations.

Preferred embodiments of the present invention will become obvious from the dependent Claims as well as the following Specification and the Examples.

DETAILED DESCRIPTION OF THE INVENTION

Since several years, the quantitative and qualitative determination of microorganisms belongs to the prior art. However, the determination of microbial contamination is particularly difficult in cases where a high concentration of other solid particles such as minerals, pigments, fillers and/or fiber materials is present in the sample to be investigated. Because these "foreign particles" often have a size similar to microorganisms, generally, it is only possible to minimize the number of such "foreign particles" by carrying out high dilutions. However, concomitantly and unavoidably, these high dilution steps reduce the number of contaminating microorganisms, and a long incubation period is required to increase the number of microorganisms by means of propagation to an extent that enables safe detection.

Therefore, there has been a need to create a new process of the type mentioned in the beginning which provides reproducible and reliable results with respect to the number, size and/or type of the microorganisms in the sample to be investigated in a substantially shorter time.

Surprisingly and unexpectedly, it has been discovered that it is possible to separate the microorganisms from inert materials ("foreign particles") by addition of degradable organic substances to the sample and performing a subsequent centrifugation. Usually, the microorganisms preferably adhere to the surface of the mineral, pigment, filler and/or fiber materials making it difficult to separate them from the surface. Although the "foreign particles" are sedimented by a simple centrifugation step, however, the microorganisms are drawn along into the pellet because they preferably adhere to those particles, and thereby the portion of microorganisms remaining in the supernatant provides incorrect values with respect to the degree of contamination with microorganisms.

It has been shown that the addition of biologically degradable organic substances surprisingly enables a separation of the microorganisms and the minerals, pigments, fillers and/or fiber materials. Preferably, the organic substance which can be degraded by microorganisms is a nutrient medium conventionally used in the cultivation of microorganisms. Surprisingly, this nutrient medium acts as a separation agent between the microorganisms and the foreign particles and, thus, for the first time enables the separation of and distinction between the two without affecting further steps of the microorganism analysis. Substances which may not be biologically degraded or whose biological degradation is difficult bear the risk that the microorganisms are separated from the inert particles while at the same time the substances act as inhibitors of microorganism growth and thus lead to inaccurate results.

In the process according to the present invention not only one process step, namely the dilution step, may be omitted but in addition the incubation period is extraordinarily reduced. Furthermore, there is not just added a separation agent but the separation agent simultaneously acts as a nutrient solution which may be employed for optimal propagation of the microorganisms to be investigated and, in a preferred embodiment, is selected to be specific for a particular microorganism type to be tested, such as bacteria, fungi or yeasts.

It was only by the addition of an organic substance which may be degraded by the microorganisms, preferably in the form of a nutrient solution or medium, respectively, and by introduction of a centrifugation step that the object according to the present invention has been solved. A reduction in analysis time or even the possibility to perform an analysis at all has been achieved because the sample to be tested contains a smaller number of "foreign particles". Moreover, it is possible to use a smaller starting number and a smaller increase in microbiological particles over time than with samples having a higher blank value, i.e. a higher number of "foreign particles".

By the process according to the invention, aqueous suspensions, emulsions and dispersions may be investigated which among other substances contain minerals, pigments, fillers and/or fiber materials, such as cellulose fibers, and which optionally further contain polymers such as natural, synthetic or semisynthetic polymers in colloidal form. Examples of such polymers are: styrene butadiene, styrene acrylate, melamine resins, formaldehyde urea resins, starch, carboxymethylcellulose.

Preferably, the samples to be tested are derived from the paper processing industry. Further areas of use are the pigment industry and the metal processing industry.

According to the present invention, a sample of the suspensions, emulsions or dispersions to be tested for microbial contamination is taken. Generally, the amount of the sample obtained is 0.5–20 ml, however, a smaller or higher amount may be taken. Besides, the amount of sample taken is not important for the success of the process of the invention.

The sample obtained is added and mixed with organic substances which may be degraded by microorganisms. The amount of biodegradable organic substances added to the sample is 0.5–50 ml of biodegradable substance per ml of sample.

The ratio of the sample volume to the volume of biodegradable substance is dependent on the original concentration of the sample and the concentration of biodegradable substance in solution. The ratio is adjusted to an amount of biodegradable substance which is large enough to enable a separation of the microorganisms and the minerals, fillers, pigments and/or fiber materials and optionally also polymers in colloidal form. The optimal ratio of the sample volume to the volume of biodegradable substance which must be determined in each case may be determined by the skilled artisan by means of manual experimentation.

Usually the concentration of the solution containing the biodegradable substance is selected to achieve a ratio of the sample solution to the solution containing the biodegradable substance of 1:0.1 to 1:100. The optimal ratio is strongly dependent on the concentration and the composition of the respective sample solution. Pigment and/or filler suspensions having a solids content of >65% by wt. are generally diluted in a ratio of 1:2 to 1:10, preferably in a ratio of 1:3. If the solids content is <65% by wt., the dilution is usually performed in a ratio of 1:0.1 to 1:1. In certain cases, especially if a very high contamination can be expected, the dilution is generally performed in a ratio of 1:10 to 1:100. The chosen dilution factor must be considered in the subsequent evaluation of the contamination or must be pointed out specifically in the result.

The biodegradable organic substances particularly include the group of nutrient media which are specific for a particular species of microorganism to be tested. Preferably, nutrient media contain a source of carbon, nitrogen, phosphate and/or sulfur as well as optionally minerals, growth factors and/or vitamins. Other substances may be added to the nutrient medium if they are required for optimal growth of the microorganisms. In the following, there are described preferred media which may be employed according to the present invention.

Optionally, following addition of the nutrient medium one or more incubation steps may be carried out to enhance the number of microorganisms in the sample. This may be especially advantageous for a subsequent qualitative analysis. In a preferred embodiment of the invention, however, this incubation prior to centrifugation is omitted leading to a marked time reduction.

To separate the microorganisms from the minerals, fillers, pigments and/or fiber materials a centrifugation step is carried out following the addition of the nutrient medium and the optional subsequent incubation step. The centrifugation step is performed in a manner to remove most of the microorganisms, i.e. more than 50%, from the "foreign particles", i.e. the minerals, fillers, pigments, polymers, and fiber materials. The centrifugation must be effective to accumulate the microorganisms in the upper phase while the foreign particles are sedimented. For this purpose, the centrifugation is preferably carried out at 100 to 1500 g, preferably 200 to 1200 g and particularly preferred at 600 to 1000 g. The gravity field is adjusted depending on the minerals, fillers, pigments, and fiber materials to be separated or depending on the microorganisms to be separated, respectively.

The optimal sedimentation index may be determined by the skilled artisan by means of experimentation. The centrifugation itself is performed for a time of 1 to 30 minutes, preferably 2 to 15 minutes and particularly preferred 5 to 10 minutes. The optimal centrifugation time may be determined by the skilled artisan performing laboratory experiments.

As the minerals and/or fillers and/or pigments there are preferably used: compounds containing elements of the second and/or third main group and/or fourth main group and/or fourth side group of the periodic system of the elements, particularly calcium and/or silicon and/or aluminium and/or titanium and/or barium and/or organic pigments.

As the minerals, fillers, and pigments, there are preferably used minerals and/or fillers and/or pigments containing kaolin and/or aluminium hydroxide and/or titanium hydroxide and/or barium sulfate and/or polystyrene hollow spheres and/or formaldehyde resins and/or calcium carbonate, particularly natural calcium carbonates and/or marble and/or lime and/or dolomite and/or calcium carbonates containing dolomite and/or synthetically prepared calcium carbonates, so-called precipitated calcium carbonated.

The supernatant containing the microorganisms is removed and may then be used directly in a quantitative and/or qualitative determination of the microbial contamination. Preferably, this is followed by one or more incubation steps to increase the number of microorganisms in the supernatant. This propagation step is performed at an incubation temperature which favors the microorganisms and is dependent on the type of microorganisms to be propagated. Preferred incubation temperatures are in the range of 20 to 37° C., further preferred 28 to 34° C., and particularly preferred 31.5 to 32.5° C. The incubation temperatures which are necessary in each case are known to the skilled artisan and may be either found in monographs or may be experimentally determined.

The total time of the individual incubation steps at an incubation temperature of 30° C. is up to 12 hours at a contamination of less than $10^5$ germs/ml of sample, up to 6 hours at a contamination of more than $10^5$ germs/ml sample but less than $10^6$ germs/g of sample, and up to 3 hours in a suspension with an original solids content of 60–80% by wt. and a contamination of more than $10^5$ germs/ml (using tryptic soy broth agar).

The sum of the individual incubation steps at 30° C. is up to 2 to 6 at a contamination of less than $10^5$ germs/ml of sample, 2 to 4 at a contamination of more than $10^5$ germs/ml sample but less than $10^6$ germs/g of sample, and 2 to 3 in a suspension with an original solids content of 60–80% by wt. and a contamination of more than $10^5$ germs/ml (using tryptic soy broth agar).

The individual incubation times at an incubation temperature of 30° C. are 1 to 12 hours at a contamination of less than $10^5$ germs/ml of sample, 1 to 6 hours at a contamination of more than $10^5$ germs/ml sample but less than $10^6$ germs/g of sample, and 1 to 2 hours in a suspension with an original solids content of 60–80% by wt. and a contamination of more than $10^5$ germs/ml (using tryptic soy broth agar).

Several methods known from the prior art are available for the quantitative or qualitative determination, respectively, of the microorganisms thus obtained. Particularly preferred according to the present invention is the CellFacts® analysis or the ATP method. Other methods are available and are known to those skilled in the art. The preferred methods are described in more detail in the following Examples.

After the process according to the present invention has been carried out, a qualitative and/or quantitative determination of the microorganisms may be performed. First, qualitative determination means a rough differentiation between the groups of fungi, yeasts and bacteria. If the CellFacts® analysis is calibrated which specific microorganisms such as specific bacteria also a further specification within individual subtypes may be performed. The qualitative analysis, for example via the CellFacts® method, is performed on the basis of a gross differentiation with respect to size or volume, respectively, of a single cell.

The type of the nutrient media employed as the separation agent particularly depends on the microorganism to be separated or propagated. Preferably, nutrient media are employed which enable the selective growth of the germs to be determined and, if possible, suppress the growth of other germs not to be determined. Examples of nutrient media which may be employed according to the present invention are tryptone azolectin/Tween 20 (TAT) broth agar, glucose solution, peptone/casein nutrient broth, preferably tryptic soy broth agar. The composition of the nutrient media is given in annex to this specification.

The concentration of the nutrient medium for the microorganisms is preferably in the range of 0.1 to 10% by wt., more advantageously 2 to 5% by wt., and particularly advantageous about 3% by wt.

The process according to the present invention not only enables a qualitative but also a quantitative determination of the bacteria, fungi and yeasts. In a preferred embodiment, this analysis is performed in one step.

Following the separation of microorganisms and minerals, fillers, pigments and/or fiber materials, i.e. the "foreign particles", one or more, preferably two to five incubation steps are carried out to increase the number of microorganisms present in the sample supernatant.

Multiple incubations are performed in intervals, i.e. the measurement of the contamination is in each case repeated after the time $t_{0+x}$. This enables the limitation of the incubation time and the incubation intervals. At the time when exponential growth is observed an extrapolation and a calculation back to the time $t_0$ is performed. Thus, a high original degree of contamination will result in a growth which can be observed and calculated earlier so that subsequent incubation intervals may be omitted.

The incubation time at a contamination of less than $10^5$ germs/ml of sample is up to 12 hours, at a contamination of less than $10^6$ germs/ml up to 6 hours, in a suspension originally containing 60–80% by wt. of solids and having a contamination of more than $10^5$ germs/ml sample up to 3 hours wherein in the last case the use of tryptic soy broth agar is preferred. The incubation time which is to be used depending on the degree of contamination with microorganisms may be determined by those skilled in the art by simple manual experimentation. The lower the original degree of microbial contamination in the sample the longer are the incubation times to be selected and vice versa. The original portion of solids in suspension does not directly affect the incubation time.

In the following, the invention will be explained in more detail with respect to comparative examples and Examples. Further modifications of the invention may be practiced by the skilled artisan on the basis of the present Specification in connection with the appended Claims as well as on the basis of assumed expertise. The invention is not limited to the present examples.

Determination of the Germ Count Using the CellFacts® Particle Counter

According to the present invention, the microorganisms of the suspension and/or emulsion and/or dispersion are aspirated by means of vacuum through a measurement pore having a defined diameter. A voltage (Volts) is applied to this pore (capillary, 30 μm). Because intact cells in a first approximation can be regarded as insulators a measurable increase in resistance is observed during passage of a cell through the measurement pore while the value of this increase is dependent on the cell volume. The current pulse is directly correlated to the volume. By incubation of the samples, small differences in the growth of the cells can be measured, i.e. cell divisions lead to a proportional increase in particle number. After observation of the exponential phase, the starting concentration may be calculated by extrapolation because the cell growth function is exponential. Due to the preparation of industrial samples according to the present invention and using the above method the determination time for $CaCO_3$, talc and kaolin slurries as well as other materials (e.g. coolants, white water, colloidal suspended starch, etc.) is in the range of only 2–12 hours instead of 24–48 hours of the prior art.

This enables timely intervention using preservatives prior to high contamination and/or spoilage of the goods.

PRIOR ART EXAMPLES

Example 1

Calcium Carbonate Slurry

A) Germ count determinations according to the Schweizerisches Lebensmittelbuch, chapter 56, section 7.01, 1985 edition, 1988 revised version, "Bestimmung von aeroben Bakterien und Keimen" and according to the Schweizerisches Lebensmittelbuch, chapter 56, section 7.22, 1985 edition, 1988 revised version, "Bestimmung von Pilzen". Proceeding 3 ml of a 77.5% by wt. aqueous slurry of natural ground marble from Norway (90% by wt. of the particles <2 μm, 65% by wt. of the particles <1 μm) dispersed with 0.65% by wt. of a commercial sodium polyacrylate were analyzed according to the method "Bestimmung von aeroben mesophilen Keimen", Schweizerisches Lebensmittelbuch, chapter 56, section 7.01, 1985 edition, 1988 revised version. Result:

After an incubation period of 48 hours the germ count determined was: $3.0 \times 10^6$ aerobic mesophilic germs/ml of suspension. No yeasts were found in the nutrient medium used for aerobic mesophilic germs. According to the method described in the Schweizerisches Lebensmittelbuch, chapter 56, section 7.22, 1985 edition, 1988 revised version, "Bestimmung von Pilzen", $<10^2$ fungi/ml were detected.

B) Determination of the Germ Count Using the CellFacts Particle Counter
Proceeding 3 ml of the 77.5% by wt. aqueous slurry of natural ground marble from Norway (90% by wt. of the particles <2 μm, 65% by wt. of the particles <1 μm) dispersed with 0.65% by wt. of a commercial sodium polyacrylate used in Example 1A) were pipetted into a sterile flask. The sample was added with 3 ml of a 3% by wt. TAT broth base/Tween 20 nutrient solution and analyzed by means of CellFacts. The analysis was performed by immediately attempting the measurement of the number of particles in the CellFacts instrument (time $t_{0h}$). Since the number of particles was much too high the instrument required a sample dilution. After a dilution of 1:10,000 had been carried out, the particle concentration was accepted by the instrument, and the blank value ($t_{0h}$) could be determined. After incubation times of 2 hrs. (time $t_{2h}$), 4 hrs. (time $t_{4h}$), after 6 hrs. (time $t_{6h}$), after 12 hrs. (time $t_{12h}$) the number of particles was again determined in the CellFacts instrument. The incubation temperature was 30° C. By plotting the number of particles against the particle diameter it is possible to determine the presence of living cells ("peak enlargement", y axis) and the type of the microorganisms, e.g. bacteria, yeasts or fungi (mean particle ø, x axis) after particular incubation times of the clear phase.

After an incubation time of 12 hours the original contamination of the suspension is evaluated by extrapolating back to the time ($t_{0h}$). As a reference, the result of Example 1A), germ count determination according to Schweizerisches Lebensmittelbuch, is used. ("Bestimmung von aeroben mesophilen Keimen", Schweizerisches Lebensmittelbuch, chapter 56, section 7.01, 1985 edition, 1988 revised version.
Result:

Germ Count Determination Using the CellFacts Particle Counter

1. Tryptic Soy Broth Agar

| Sample | Extraction agent | Determination time in hrs. | Aerobic mesophilic germs/ml of suspension (peak max. at particle Ø of 1–2.5 μm) |
|---|---|---|---|
| 1 | Tryptic soy broth agar | 12 | <$10^2$ |

| Sample | Extraction agent | Determination time in hrs. | fungi/ml of suspension (peak max. at particle Ø of 5–9 μm) |
|---|---|---|---|
| 1 | Tryptic soy broth agar | 12 | <$10^2$ |

It becomes clear from Examples 1A) and 1B) that using the methods of the prior art it is impossible to perform a determination of bacteria, fungi and yeasts in the above suspension by means of the CellFacts instrument, and that particularly at <$10^2$ germs/ml a completely inaccurate result is obtained. Furthermore, the determination according to the method of the Schweizerisches Lebensmittelbuch requires 48 hrs.

Presumably, by the sample dilution required in the CellFacts instrument also the microbiological germs present were diluted to below the detection limit.

Performing the determination according to the Schweizerisches Lebensmittelbuch the duration of the analysis is 48 hrs.

C) Germ Count Determination by ATP Measurement
Proceeding 3 ml of the sample of Example 1A), 77.5% by wt. aqueous slurry of natural ground marble from Norway (90% by wt. of the particles <2 μm, 65% by wt. of the particles <1 μm) dispersed with 0.65% by wt. of a commercial sodium polyacrylate, were pipetted into a sterile flask. The sample was added with 3 ml of a 3% by wt. TAT broth base/Tween 20 nutrient solution and analyzed by means of the BioOrbit lunimometer 1253. The analysis was performed by immediately attempting the measurement of the amount of light released by ATP in the BioOrbit luminometer 1253 (time $t_{0h}$). In addition, a sample was measured after performing a 1:10,000 dilution. In this manner, the blank value ($t_{0h}$) was determined in each case. After incubation times of 4 hrs. (time $t_{4h}$), after 7 hrs. (time $t_{7h}$), and after 17 hrs. (time $t_{17h}$) measurements of the light intensity in the BioOrbit 1253 luminometer were carried out. The incubation temperature was 30° C. By plotting the light intensity at the respective incubation time against the incubation time it is possible to determine the presence of living cells (increase in light intensity over time). After an incubation time with nearly exponential growth the contamination of the suspension may be determined comparatively by comparing the progression of the curves of the individual samples. By this, a semi-quantitative distinction may be made between "no growth", "weak growth", and "strong growth".

Proceeding of the Measurement in the Luminometer 1253 a) Initially, 100 μl of each of the samples prepared as described above are pipetted into a luminometer cuvette.

b) To this, 100 μl of ATP releasing reagent are added, shook well and left for one minute so that the ATP may be removed by extraction.

c) Afterwards, 500 μl of AMR reagent are added and mixed by shaking.

d) Then, the cuvette may be introduced into the measurement cell and readings of the light emission may be performed.

Reference: User's manual of the BioOrbit luminometer ver. 3.0, May 95 as well as Application Note 20 of BioOrbit OY company, FIN 20521 Turku, Finland.

Result:

| Incubation time in hours | Sample light intensity [RLU] on the LCD display | Sample 1:10,000 dilution, light intensity [RLU] on the LCD display |
|---|---|---|
| 0 | 0.001 | 0.002 |
| 4 | 0.000 | 0.001 |
| 7 | 0.002 | 0.002 |
| 17 | 0.001 | 0.001 |

After 17 hours, no differences between the individual incubation times can be observed using this prior art method, i.e. it has to be assumed that the slurry is not contaminated. However, the same slurry has been used in Example 1A) (method according to Schweizerisches Lebensmittelbuch), and since this appreciated method used in the Example gives a result of $3 \times 10^6$ germs/ml it becomes obvious that the result of the present Example 1C) must be erroneous. In practice, this would entail fatal consequences such as food poisoning or spoilage of goods.

Using the methods of the prior art, it is impossible to determine bacteria, fungi and yeasts in the above-mentioned suspension.

Presumably, the high particle concentration in the original concentration of the suspension resulted in complete light adsorption of the amount of light released by ATP in the suspension, and sample dilution by this method also led to a dilution of the microbiological germs present to below the detection limit thereof.

INVENTIVE EXAMPLES

Example 2

Calcium Carbonate Slurry, Analysis Instrument CellFacts Measuring Instrument

Proceeding 3 ml each of the 77.5% by wt. aqueous slurry of natural ground marble from Norway (90% by wt. of the particles <2 μm, 65% by wt. of the particles <1 μm) dispersed with 0.65% by wt. of a commercial sodium polyacrylate are pipetted into separate sterile flasks. One sample is added with 3 ml of a 3% by wt. TAT broth base/Tween 20 nutrient solution and the second sample with 3 ml of a 3% by wt. tryptic soy broth nutrient solution. Afterwards, both of the samples are mixed well for 20 sec. and then centrifuged. After a centrifugation for 10 min at 800 g the clear supernatant phase is isolated and analyzed by means of CellFacts. The analysis is performed by measuring the number of particles in the CellFacts instrument immediately after centrifugation (time $t_{0h}$), after incubation times of 2 hrs. (time $t_{2h}$), 4 hrs. (time $t_{4h}$), and after 6 hrs. (time $t_{6h}$). The incubation temperature was 30° C. By plotting the number of particles against the particle diameter it is possible to determine the presence of living cells (peak enlargement) and the type of the microorganisms (bacteria, yeasts or fungi) after particular incubation times of the clear phase. After an incubation time with exponential growth the original contamination of the suspension is determined by extrapolating back to the time $t_{0h}$. In comparison, the germ count determination according to the Schweizerisches Lebensmittelbuch is performed. ("Bestimmung von aeroben mesophilen Keimen", Schweizerisches Lebensmittelbuch, chapter 56, section 7.01, 1985 edition. 1988 revised version).

Results:

Germ Count Determination According to the Schweizerisches Lebensmittelbuch

The germ count determination after 48 hours revealed: $3.0 \times 10^6$ aerobic mesophilic germs/ml of suspension Germ Count Determination Using the CellFacts Particle Counter 1. TAT broth base/Tween 20 (polyoxyethylene sorbitan monolaurate)

2. Tryptic soy broth agar

| Sample | Extraction agent | Required Determination time in hrs. | Aerobic mesophilic germs/ml of suspension (peak max. at particle Ø of 1–2.5 μm) |
|---|---|---|---|
| 1 | TAT broth base/ Tween 20 | 6 | $1.25 \times 10^6$ |
| 2 | Tryptic soy broth agar | 4 | $3.14 \times 10^6$ |

| Sample | Extraction agent | Determination time in hrs. | fungi/ml of suspension (peak max. at particle Ø of 5–9 μm) |
|---|---|---|---|
| 2 | Tryptic soy broth agar | 12 | $<10^2$ |

The samples analyzed according to the method of the present invention are in excellent accordance with the determination of the germ count according to the Schweizerisches Lebensmittelbuch determined after 48 hours. Compared to the determination of the germ count according to the Schweizerisches Lebensmittelbuch both samples are very well within the confidence limits.

Confidence limits, as used herein, is intended to mean a deviation of ±0.5 $\log_{10}$ of individual germ count determinations as established by the PHLS Central Public Health Laboratory, 61 Colindale Avenue, London NW9 5HT, UK, distribution 070, pages 6 and 7 and appendix 1, distribution date Nov. 16, 1998, report date Dec. 30, 1998.

Example 3

Calcium Carbonate Slurry, Analysis Device BioOrbit 1253 Luminometer

Proceeding 500 ml each of a 71.5% by wt. aqueous slurry of natural ground marble (90% by wt. of the particles <2 μm, 65% by wt. of the particles <1 μm) dispersed with 0.5% by wt. of a commercial sodium polyacrylate, were charged into 1 l glass flasks. One of the samples was stored for 3 days at 5° C. (sample A), the other was stored for 3 days at 30° C. (sample B). Afterwards, the samples were brought to 20° C., and 3 ml of each of the samples were mixed well with 3 ml of the respective extraction agent in sterile flasks. Following a centrifugation for 10 min at 600 g the clear supernatant phase is isolated and analyzed for light emission by means of the BioOrbit lunimometer 1253. The analysis is performed by measuring the light intensity in the BioOrbit luminometer 1253 immediately after centrifugation (time $t_{0h}$), after 4 hrs. (time $t_{4h}$), after 7 hrs. (time $t_{7h}$), after 17 hrs. (time $t_{17h}$). The incubation temperature was 30° C. By plotting the light intensity after the respective incubation time against the incubation time it is possible to determine the presence of living cells (increase in light intensity over time) in the clear phase. After an incubation time with nearly exponential growth the contamination of the suspension may be determined comparatively by comparing the progression of the curves of the individual samples. By this, a semi-quantitative distinction may be made between "no growth", "weak growth", and "strong growth". In comparison, a germ count determination according to the Schweizerisches Lebensmittelbuch was performed. ("Bestimmung von aeroben mesophilen Keimen", Schweizerisches Lebensmittelbuch, chapter 56, section 7.01, 1985 edition. 1988 revised version).

Extraction agents used:

1. Prior art, 0.9% by wt. solution of NaCl in Aq. dest. without organic substance that may serve as a nutrient 2. According to the invention, 3% by wt. organic nutrient solution (tryptic soy broth agar)

Germ Count Determination According to the Schweizerisches Lebensmittelbuch

Sample A: $5 \times 10^4$ aerobic mesophilic germs/g of suspension after 48 hours Sample B: $7 \times 10^7$ aerobic mesophilic germs/g of suspension after 48 hours Results:

Evaluation of the contamination with the BioOrbit luminometer

Prior art, 0.9% by wt. solution of NaCl in Aq. dest.

| Incubation time in hours | Sample 1A, light intensity [RLU] on the LCD display | Sample 1B, light intensity [RLU] on the LCD display |
|---|---|---|
| 0 | 0.001 | 0.001 |
| 4 | 0.002 | 0.003 |
| 7 | 0.002 | 0.004 |
| 17 | 0.004 | 0.007 |

Using the prior art method, no clear difference is observed between the weakly and the strongly contaminated suspension after 17 hours.

According to the present invention, 3% by wt. organic nutrient solution (tryptic soy broth agar)

| Incubation time in hours | Sample 1A, light intensity [RLU] on the LCD display | Sample 1B, light intensity [RLU] on the LCD display |
|---|---|---|
| 0 | 0.001 | 0.002 |
| 4 | 0.004 | 0.006 |
| 7 | 0.007 | 0.045 |
| 17 | 0.050 | 0.240 |

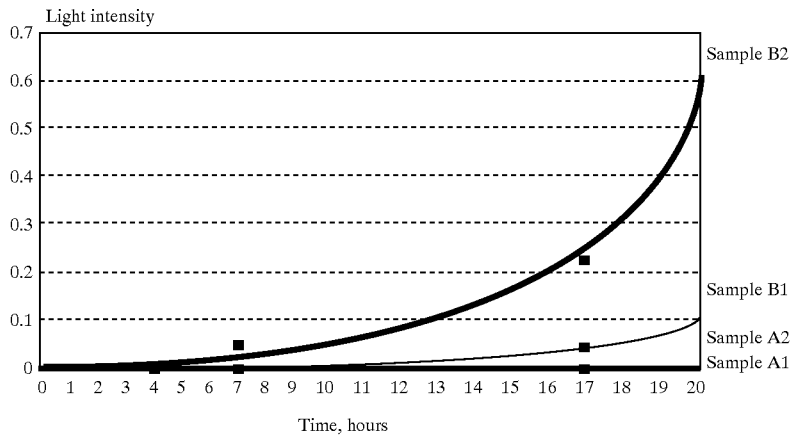

Using the novel method according to the present invention, it is possible to distinguish between "weakly" and "strongly contaminated" solutions already after 7 hours. In addition, a "weak contamination" may be significantly detected already after 17 hours.

The literature and the user's manual of the BioOrbit luminometer ver. 3.0, May 95 as well as "application note 20" of BioOrbit OY company, FIN 20521 Turku, Finland, also show evaluation models for the calculation of the biomass using the [RLU] values. Furthermore, the germ count/ml may be determined by "calibration" using suspensions with a known degree of contamination.

Example 4

US Clay Slurry

Proceeding 3 ml each of a 72.8% by wt. aqueous slurry of natural ground US clay from Georgia USA (95% by wt. of the particles <2 μm, 78% by wt. of the particles <1 μm) dispersed with 0.35% by wt. of a commercial sodium polyacrylate are pipetted into separate sterile flasks. One sample is added with 3 ml of a 3% by wt. TAT broth base/Tween 20 nutrient solution and the second sample with 3 ml of a 3% by wt. tryptic soy broth nutrient solution. Afterwards, both of the samples are mixed well for 20 sec. and then centrifuged. After a centrifugation for 10 min at 800 g the clear supernatant phase is isolated and analyzed by means of CellFacts. The analysis is performed by measuring the number of particles in the CellFacts instrument immediately following centrifugation (time $t_{0h}$), after incubation times of 2 hrs. (time $t_{2h}$), 4 hrs. (time $t_{4h}$), after 6 hrs. (time $t_{6h}$), and after 12 hrs. (time $t_{12h}$). The incubation temperature was 30° C. By plotting the number of particles against the diameter of these particles it is possible to determine the presence of living cells (peak enlargement) and the species of the microorganisms (bacteria, yeasts or fungi) after particular incubation times of the clear phase. After an incubation time with nearly exponential growth the original contamination of the suspension is determined by extrapolating back to the time $t_{0h}$. In comparison, a germ count determination according to the Schweizerisches Lebensmittelbuch is performed. ("Bestimmung von aeroben mesophilen Keimen", Schweizerisches Lebensmittelbuch, chapter 56, section 7.01, 1985 edition. 1988 revised version).

Germ Count Determination According to the Schweizerisches Lebensmittelbuch

The germ count determination after 48 hours revealed: $5.0 \times 10^5$ aerobic mesophilic germs/ml of suspension Germ Count Determination Using the CellFacts Particle Counter 1. TAT broth base/Tween 20 (polyoxyethylene sorbitan monolaurate)
2. Tryptic soy broth agar

| Sample | Extraction agent | Required Determination time in hrs. | Aerobic mesophilic germs/ml of suspension (peak max. at particle Ø of 1–2.5 µm) |
|---|---|---|---|
| 1 | TAT broth base/ Tween 20 | 12 | $1.12 \times 10^5$ |
| 2 | Tryptic soy broth agar | 6 | $5.21 \times 10^5$ |

| Sample | Extraction agent | Determination time in hrs. | fungi/ml of suspension (peak max. at particle Ø of 5–9 µm) |
|---|---|---|---|
| 2 | Tryptic soy broth agar | 12 | approx. $10^3$ |

The samples analyzed according to the method of the present invention are in excellent accordance with the determination of the germ count according to the Schweizerisches Lebensmittelbuch determined after 48 hours. Compared to the determination of the germ count according to the Schweizerisches Lebensmittelbuch both samples are very well within the confidence limits.

Confidence limits, as used herein, is intended to mean a deviation of ±0.5 $\log_{10}$ of individual germ count determinations as established by the PHLS Central Public Health Laboratory, 61 Colindale Avenue, London NW9 5HT, UK, distribution 070, pages 6 and 7 and appendix 1, distribution date Nov. 16, 1998, report date Dec. 30, 1998.

Example 5

Paper Making Machine White Water Proceeding 3 ml of a 0.5% by wt. aqueous slurry containing about 0.2% by wt. of natural ground marble from Norway (60% by wt. of the particles <2 µm, 35% by wt. of the particles <1 µm) dispersed with 0.15% by wt. of a commercial sodium polyacrylate and about 0.3% by wt. of cellulose fibers (sulfite/sulfate paper pulp) as it is used in paper mills for paper making and about 0.05% by wt. of a commercial polyacrylamide are pipetted into a sterile flask. The sample is added with 3 ml of a 3% by wt. tryptic soy broth nutrient solution. Afterwards, the sample is mixed well for 20 sec. and then centrifuged. After a centrifugation for 10 min at 1000 g the clear supernatant phase is isolated and analyzed by means of CellFacts. The analysis is performed by measuring the number of particles in the CellFacts instrument immediately following centrifugation (time $t_{0h}$), after incubation times of 1 hr. (time $t_{1h}$), 2 hrs. (time $t_{2h}$). The incubation temperature was 30° C. By plotting the number of particles against the diameter of these particles it is possible to determine the presence of living cells (peak enlargement) and the species of the microorganisms (bacteria, yeasts or fungi) after particular incubation times of the clear phase. After an incubation time with nearly exponential growth the original contamination of the suspension is determined by extrapolating back to the time $t_{0h}$. In comparison, a germ count determination according to the Schweizerisches Lebensmittelbuch is performed. ("Bestimmung von aeroben mesophilen Keimen", Schweizerisches Lebensmittelbuch, chapter 56, section 7.01, 1985 edition. 1988 revised version).

Germ Count Determination According to the Schweizerisches Lebensmittelbuch

The germ count determination after 48 hours revealed: $3.0 \times 10^7$ aerobic mesophilic germs/ml of suspension Germ Count Determination Using the CellFacts Particle Counter 1. Tryptic soy broth agar

| Sample | Extraction agent | Required Determination time in hrs. | Aerobic mesophilic germs/ml of suspension (peak max. at particle Ø of 1–2.5 µm) |
|---|---|---|---|
| 1 | Tryptic soy broth agar | 2 | $3.45 \times 10^7$ |

| Sample | Extraction agent | Determination time in hrs. | fungi/ml of suspension (peak max. at particle Ø of 5–9 µm) |
|---|---|---|---|
| 1 | Tryptic soy broth agar | 6 | approx. $10^4$ |

The samples analyzed according to the method of the present invention are in excellent accordance with the determination of the germ count according to the Schweizerisches Lebensmittelbuch determined after 48 hours. Compared to the determination of the germ count according to the Schweizerisches Lebensmittelbuch both samples are very well within the confidence limits.

Confidence limits, as used herein, is intended to mean a deviation of ±0.5 $\log_{10}$ of individual germ count determinations as established by the PHLS Central Public Health Laboratory, 61 Colindale Avenue, London NW9 5HT, UK, distribution 070, pages 6 and 7 and appendix 1, distribution date Nov. 16, 1998, report date Dec. 30, 1998.

Example 6

Colloidal Starch Suspension

Proceeding 3 ml of a 10% by wt. aqueous colloidal corn starch suspension as employed in paper mills are pipetted into a sterile flask. The sample is added with 3 ml of a 3% by wt. tryptic soy broth nutrient solution. Afterwards, the sample is mixed well for 20 sec. and then centrifuged. After a centrifugation for 10 min at 800 g the clear supernatant phase is isolated and analyzed by means of CellFacts. The analysis is performed by measuring the number of particles in the CellFacts instrument immediately following centrifugation (time $t_{0h}$), after incubation times of 1 hr. (time $t_{1h}$), 2 hrs. (time $t_{2h}$). The incubation temperature was 30° C. By plotting the number of particles against the diameter of these particles it is possible to determine the presence of living cells (peak enlargement) and the species of the microorganisms (bacteria, yeasts or fungi) after particular incubation times of the clear phase. After an incubation time with nearly exponential growth the original contamination of the suspension is determined by extrapolating back to the time $t_{0h}$. In comparison, a germ count determination according to the Schweizerisches Lebensmittelbuch is performed. ("Bestimmung von aeroben mesophilen Keimen", Schweizerisches Lebensmittelbuch, chapter 56, section 7.01, 1985 edition. 1988 revised version).

Germ Count Determination According to the Schweizerisches Lebensmittelbuch

The germ count determination after 48 hours revealed: $4.0 \times 10^6$ aerobic mesophilic germs/ml of suspension

Germ Count Determination Using the CellFacts Particle Counter

1. Tryptic soy broth agar

| Sample | Extraction agent | Required Determination time in hrs. | Aerobic mesophilic germs/ml of suspension (peak max. at particle Ø of 1–2.5 μm) |
|---|---|---|---|
| 1 | Tryptic soy broth agar | 2 | $4.22 \times 10^6$ |

| Sample | Extraction agent | Determination time in hrs. | fungi/ml of suspension (peak max. at particle Ø of 5–9 μm) |
|---|---|---|---|
| 1 | Tryptic soy broth agar | 12 | $<10^2$ |

The sample analyzed according to the method of the present invention are in excellent accordance with the determination of the germ count according to the Schweizerisches Lebensmittelbuch determined after 48 hours. Compared to the determination of the germ count according to the Schweizerisches Lebensmittelbuch both samples are very well within the confidence limits.

Confidence limits, as used herein, is intended to mean a deviation of $\pm 0.5 \log_{10}$ of individual germ count determinations as established by the PHLS Central Public Health Laboratory, 61 Colindale Avenue, London NW9 5HT, UK, distribution 070, pages 6 and 7 and appendix 1, distribution date Nov. 16, 1998, report date Dec. 30, 1998.

Example 7

Proceeding 3 ml each of a 71.5% by wt. aqueous slurry of natural ground marble (90% by wt. of the particles <2 μm, 65% by wt. of the particles <1 μm) dispersed with 0.5% by wt. of a commercial sodium polyacrylate are mixed well in sterile flasks with 3 ml each of the respective extraction agent. After a centrifugation for 10 min at 800 g the clear supernatant phase is isolated and analyzed by means of CellFacts. The analysis is performed by measuring the number of particles in the CellFacts instrument immediately following centrifugation (time $t_{0h}$), after incubation times of 2 hrs. (time $t_{2h}$), 4 hrs. (time $t_{4h}$), after 7 hrs. (time $t_{7h}$), after 17 hrs. (time $t_{17h}$), and after 24 hrs. (time $t_{24h}$). The incubation temperature was 30° C. By plotting the number of particles against the diameter of these particles it is possible to determine the presence of living cells (peak enlargement) and the species of the microorganisms (bacteria, yeasts or fungi) after particular incubation times of the clear phase. After an incubation time with nearly exponential growth the original contamination of the suspension is determined by extrapolating back to the time $t_{0h}$. In comparison, a germ count determination according to the Schweizerisches Lebensmittelbuch is performed. ("Bestimmung von aeroben mesophilen Keimen", Schweizerisches Lebensmittelbuch, chapter 56, section 7.01, 1985 edition. 1988 revised version).

Extraction agents used:

Prior Art

1. Aq. dest.
2. 0.9% by wt. NaCl solution in Aq. dest., inorganic salt
3. 0.8% by wt. solution of polyoxyethylene sorbitan monolaurate (2 moles of polyoxyethylene), organic surfactant

Example According to the Present Invention 4. 3% by wt. of organic nutrient solution (tryptic soy broth agar)

Germ Count Determination According to the Schweizerisches Lebensmittelbuch

The germ count determination after 48 hours revealed: $5.0 \times 10^4$ aerobic mesophilic germs/ml of suspension

Germ Count Determination Using the CellFacts Particle Counter

| Sample | Extraction agent | Required Determination time in hrs. | Aerobic mesophilic germs/ml of suspension (peak max. at particle Ø of 1–2.5 μm) |
|---|---|---|---|
| 1 | Aq. dest. | 17 | $2 \times 10^3$ |
| 2 | NaCl solution | 18 | $1.6 \times 10^3$ |

-continued

| Sample | Extraction agent | Required Determination time in hrs. | Aerobic mesophilic germs/ml of suspension (peak max. at particle Ø of 1–2.5 μm) |
|---|---|---|---|
| 3 | polyoxyethylene sorbitan monolaurate | 24 | >$10^2$ |
| 4 | organic nutrient solution | 7 | $5,6 \times 10^4$ |

The samples 1–3 first clearly demonstrate that a very long incubation time is required until a result can be calculated and, second, that also this result is incorrect. (Reference: determination of the germ count according to the Schweizerisches Lebensmittelbuch)

For samples 1–3, the variation to the germ count determined according to the Schweizerisches Lebensmittelbuch is far beyond the confidence limit.

Samples 1 and 2 lack an organic substance which may act as a nutrient. Sample 3 contains an organic substance. However, this substance is not active as a nutrient but rather as an inhibitor. A certain inhibition by Tween 20 can already be observed in Example 4-1 where Tween 20 has been employed if the result is compared to Example 4-2. However, the organic substance acting as a nutrient solution employed according to the present invention was able to prevent an incorrect result in the case of Example 4-2. However, in comparison to Example 7-4, the Example 7-3 gives fatal erroneous result!

Sample 4 which has been analyzed according to the method of the present invention is in excellent accordance with the germ count determination according to the Schweizerisches Lebensmittelbuch.

In sample 4, the difference to the germ count determination according to the Schweizerisches Lebensmittelbuch is very well within the confidence limits.

Confidence limits, as used herein, is intended to mean a deviation of ±0.5 $\log_{10}$ of individual germ count determinations as established by the PHLS Central Public Health Laboratory, 61 Colindale Avenue, London NW9 5HT, UK, distribution 070, pages 6 and 7 and appendix 1, distribution date Nov. 16, 1998, report date Dec. 30, 1998.

Composition of Preferred Nutrient Media

| Tryptic Soy Broth | |
|---|---|
| Bacto tryptone | 17.0 g/l |
| Bacto soytone | 3.0 g/l |
| Bacto dextrose | 2.5 g/l |
| sodium chloride | 5.0 g/l |
| dipotassium phosphate | 2.5 g/l |

| TAT Broth Base | |
|---|---|
| Bacto tryptone | 20.0 g/l |
| azolectin | 5.0 g/l |

| Nutrient Broth | |
|---|---|
| Bacto beef extract | 3.0 g/l |
| Bacto peptin | 5.0 g/l |

| Peptin from casein, tryptic digest | |
|---|---|
| peptin from casein | 1.0 g/l |
| sodium chloride | 1.8 g/l |

| Plate Count Agar | |
|---|---|
| Bacto tryptone | 5.0 g/l |
| yeast extract | 2.5 g/l |
| Bacto dextrose | 1.0 g/l |
| Agar No. 1 | 9.0 g/l |

| Ethylene Glycol | |
|---|---|
| ethylene glycol | 1.0 g/l |
| azolectin | 5.0 g/l |
| sodium chloride | 1.8 g/l |

| Glycerol | |
|---|---|
| glycerol | 1.0 g/l |
| azolectin | 5.0 g/l |
| sodium chloride | 1.8 g/l |

What is claimed is:

1. A method for the quantitative or qualitative determination of microbial contamination of a suspension, emulsion, or dispersion comprising a mineral, pigment, filler, fiber material, or combinations thereof, the method comprising:

(a) mixing a sample of the suspension, emulsion, or dispersion with an amount of one or more organic substances which can be degraded by a microorganism and which is effective as a separating agent between the microorganism and the mineral, pigment, filler, fiber material, or combinations thereof, wherein the amount of one or more organic substances is selected such that a separation of the microorganism from the mineral, filler, pigment, fiber material, or combinations thereof is rendered possible;

(b) centrifuging the mixture obtained in step (a) so that a majority of the mineral, filler, pigment, fiber material, or combinations thereof is separated from the microorganism and the microorganism is in the upper phase;

(c) separating the upper phase as an aqueous supernatant; and (d) determining the number, size, type, or combinations thereof, of the microorganism in the supernatant.

2. The method according to claim 1, further comprising performing an incubation in step (a) to increase the number of the microorganism.

3. The method of claim 2, wherein the incubation temperature is 20–37° C.

4. The method of claim 3, wherein the incubation temperature is 28–34° C.

5. The method of claim 4, wherein the incubation temperature is 31.5–32.5° C.

6. The method of claim 1, wherein the microbial contamination is selected from the group consisting of bacteria, fungi, yeasts, and combinations thereof.

7. The method of claim 6, wherein the determination of bacteria, fungi, yeasts, and combinations thereof is qualitative or quantitative and is performed simultaneously in one analysis.

8. The method of claim 1, further comprising subjecting the aqueous supernatant of step (c) to one or more incubations in order to increase the number of the microorganism in the supernatant.

9. The method of claim 1, wherein the one or more organic substances is added in the form of a nutrient medium for microorganisms.

10. The method of claim 9, wherein the nutrient medium comprises a source of carbon, nitrogen, phosphate, sulphur, or combinations thereof.

11. The method of claim 9, wherein the nutrient medium further comprises a mineral, a growth factor, a vitamin, or combinations thereof.

12. The method of claim 1, wherein the centrifugation is performed at 100–1,500 g.

13. The method of claim 12, wherein the centrifugation is performed at 200–1,200 g.

14. The method of claim 13, wherein the centrifugation is performed at 600–1,000 g.

15. The method of claim 1, further comprising using a nutrient medium that enables the selective growth of the microorganism to be determined.

16. The method of claim 15, wherein the nutrient medium is selected from the group consisting of tryptone azolectin/ Tween 20 broth agar, glucose solution, peptone/casein, nutrient broth, and combinations thereof.

17. The method of claim 16, wherein the nutrient broth is tryptic soy broth agar.

18. The method of claim 1, wherein the concentration of the nutrient medium is 0.1–10% by weight.

19. The method of claim 18, wherein the concentration of the nutrient medium is 2–5% by weight.

20. The method of claim 19, wherein the concentration of the nutrient medium is 3% by weight.

21. The method of claim 1, wherein the suspension, emulsion, or dispersion further comprises a polymer in a colloidal form.

22. The method of claim 1, wherein the centrifugation step is performed for a time of 1–30 minutes.

23. The method of claim 22, wherein the centrifugation step is performed for a time of 2–15 minutes.

24. The method of claim 23, wherein the centrifugation step is performed for a time of 10 minutes.

25. The method of claim 1, further comprising analyzing the upper phase obtained by centrifugation containing the microorganism for the number of the microorganism by a particle size analysis method.

26. The method of claim 25, wherein the size and number of the microorganism are analyzed by aspirating the microorganism sampled using a vacuum through a measurement pore having a defined length and diameter, wherein a voltage is applied at the pore inlet and exit and a current pulse is measured upon passage of the microorganism through the sample which is directly correlated to the volume of the microorganism, and the number of pulses is correlated to the number of the microorganism.

27. The method of claim 1, further comprising analyzing the upper phase obtained by centrifugation containing the microorganism for the number of microorganisms by determining an amount of ATP produced by the microorganisms.

28. A method of investigating the microbial contamination of a dispersion, emulsion, or suspension in a metal industry, pigment and paper industry, or paper industry white waters, the method comprising:

(a) mixing a sample of the suspension, emulsion, or dispersion with an amount of one or more organic substances which can be degraded by a microorganism and which is effective as a separating agent between the microorganism and a mineral, pigment, filler, fiber material, or combinations thereof, wherein the amount of the one or more organic substances is selected in a manner that a separation of the microorganism from the mineral, filler, pigment, fiber material, or combinations thereof is rendered possible;

(b) subjecting the mixture thus obtained to centrifugation so that a majority of the mineral, filler, pigment, fiber material, or combinations thereof is separated from the microorganism and the microorganism is in the upper phase;

(c) separating the upper phase as an aqueous supernatant; and (d) determining the number, size, type, or combinations thereof, of the microorganism in the supernatant.

* * * * *